United States Patent [19]

Mylchreest et al.

[11] Patent Number: 5,157,260
[45] Date of Patent: Oct. 20, 1992

[54] METHOD AND APPARATUS FOR FOCUSING IONS IN VISCOUS FLOW JET EXPANSION REGION OF AN ELECTROSPRAY APPARATUS

[75] Inventors: Iain C. Mylchreest, Santa Clara; Mark E. Hail, Alameda, both of Calif.; John R. Herron, Linn County, Oreg.

[73] Assignee: Finnian Corporation, San Jose, Calif.

[21] Appl. No.: 702,634

[22] Filed: May 17, 1991

[51] Int. Cl.⁵ .............................. H01J 49/04
[52] U.S. Cl. .................. 250/423 R; 250/281; 250/288
[58] Field of Search .............. 250/423 R, 281, 282, 250/288, 288 A, 396 R; 315/111.81; 313/361.1, 362.1

[56] References Cited

U.S. PATENT DOCUMENTS

| | | | |
|---|---|---|---|
| 3,233,404 | 2/1966 | Huber et al. | 313/362.1 |
| 4,023,398 | 5/1977 | French et al. | 75/23 |
| 4,121,099 | 10/1978 | French et al. | 250/296 |
| 4,137,750 | 2/1979 | French et al. | 73/23 |
| 4,144,451 | 3/1979 | Kambara | 250/281 |
| 4,209,696 | 6/1980 | Fite | 250/288 A |
| 4,298,795 | 11/1981 | Takeuchi et al. | 250/288 |
| 4,318,028 | 3/1982 | Perel et al. | 315/111.81 |
| 4,531,056 | 7/1985 | Labowsky et al. | 250/288 |
| 4,542,293 | 9/1985 | Fenn et al. | 250/288 |
| 4,842,701 | 6/1989 | Smith et al. | 250/288 |
| 4,861,988 | 8/1989 | Henion et al. | 290/288 |
| 4,882,485 | 11/1989 | Duryea | 250/288 |
| 4,977,320 | 12/1990 | Chowdhury et al. | 250/288 |

Primary Examiner—Jack I. Berman
Assistant Examiner—Kiet T. Nguyen
Attorney, Agent, or Firm—Flehr, Hohbach, Test, Albritton & Herbert

[57] ABSTRACT

An electrospray ion source having a capillary tube for directing ions from an ionizing region to an analyzing region where it forms a gas jet with ions which expands and a tube lens cooperating with said capillary for forcing ions to the center of said jet.

4 Claims, 2 Drawing Sheets

FIG.—1

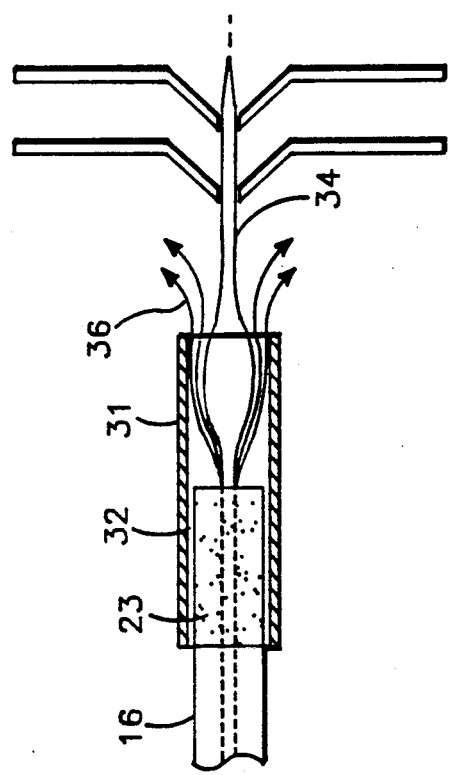
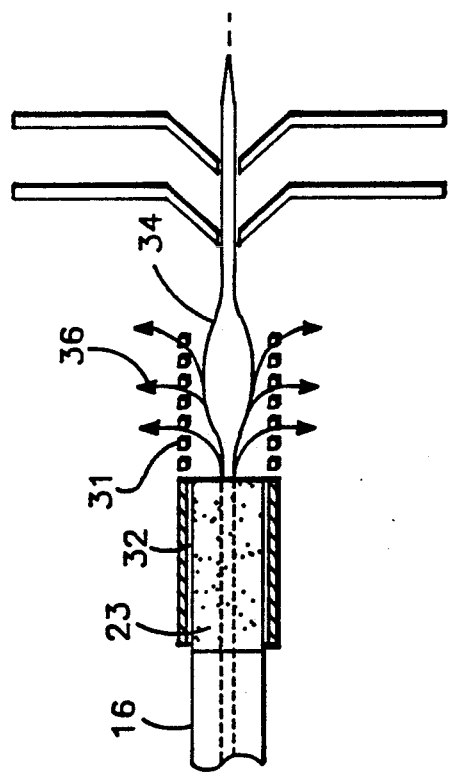
FIG.-2
FIG.-3

METHOD AND APPARATUS FOR FOCUSING IONS IN VISCOUS FLOW JET EXPANSION REGION OF AN ELECTROSPRAY APPARATUS

BRIEF DESCRIPTION OF THE INVENTION

This invention relates generally to electrospray ion sources and more particularly to such sources which include means for focusing the ions in the viscous flow expansion region.

BACKGROUND OF THE INVENTION

In electrospray ionization, ions are formed in an ionizing region which is generally at atmospheric pressure and are drawn into a low pressure region through an orifice or tube where they undergo a viscous jet flow expansion. A skimmer is generally located adjacent the tube orifice and passes ions flowing along the axis to a lower pressure analyzing region. Electrospray ionizing assemblies are described in U.S. Pat. Nos. 4,121,099; 4,861,988; 4,137,750; 4,531,056 and 4,542,293. U.S. Pat. Nos. 4,861,988 and 4,121,099 disclose focusing of the ions after they enter the low pressure region. In U.S. Pat. No. 4,861,988 the ions are focused by a cylindrical member located in the analyzing region and following skimmers. In U.S. Pat. No. 4,121,099 a conical member spaced from an aperture which communicates between the ionization region and a lower pressure region.

In U.S. Pat. No. 4,542,293 there is described the use of a capillary tube made of an electrical insulator for conducting ions in the ionizing electrospray region at atmospheric pressure and a low pressure region. A glass or quartz capillary is suitable. Ions and gas are caused to flow from the ionization region through the tube into the low pressure region where free jet expansion occurs. A conductive coating is formed on the ends of the insulating tube and a voltage is applied thereacross to accelerate ions which flow through the tube. A conducting skimmer is disposed adjacent the end of the tube and is maintained at a voltage which causes further acceleration of the ions through and into a lower pressure region including focusing lenses and analyzing apparatus.

When the gas with entrained ions undergoes free expansion, the center of the flow is skimmed by the skimmer. However, a high percentage of the ions escape and are not captured by the skimmer.

OBJECTS AND SUMMARY OF THE INVENTION

It is a general object of this invention to provide an electrospray apparatus which provides improved ion capture.

It is another object of the invention to provide an electrospray apparatus in which a tube lens concentrates the ions at the center of the jet flow where they are captured by the skimmer.

The foregoing and other objects of this invention are achieved by placing a conductive tube lens in cooperation with the end of the capillary tube which directs the gas with entrained ions from the ionization region into the low pressure region and applying a voltage between the end of the capillary tube and tube lens to set up electric fields which concentrate the ions at the center of the jet flow.

BRIEF DESCRIPTION OF THE DRAWINGS

The foregoing and other objects of the invention will be more clearly understood from the description to follow when read in conjunction with the accompanying drawings of which:

FIG. 2 is an enlarged view of the region 2—2 of FIG. 1; and

FIG. 3 is another embodiment of the tube lens shown in FIGS. 1 and 2.

DETAILED DESCRIPTION OF THE INVENTION

Figure 1:
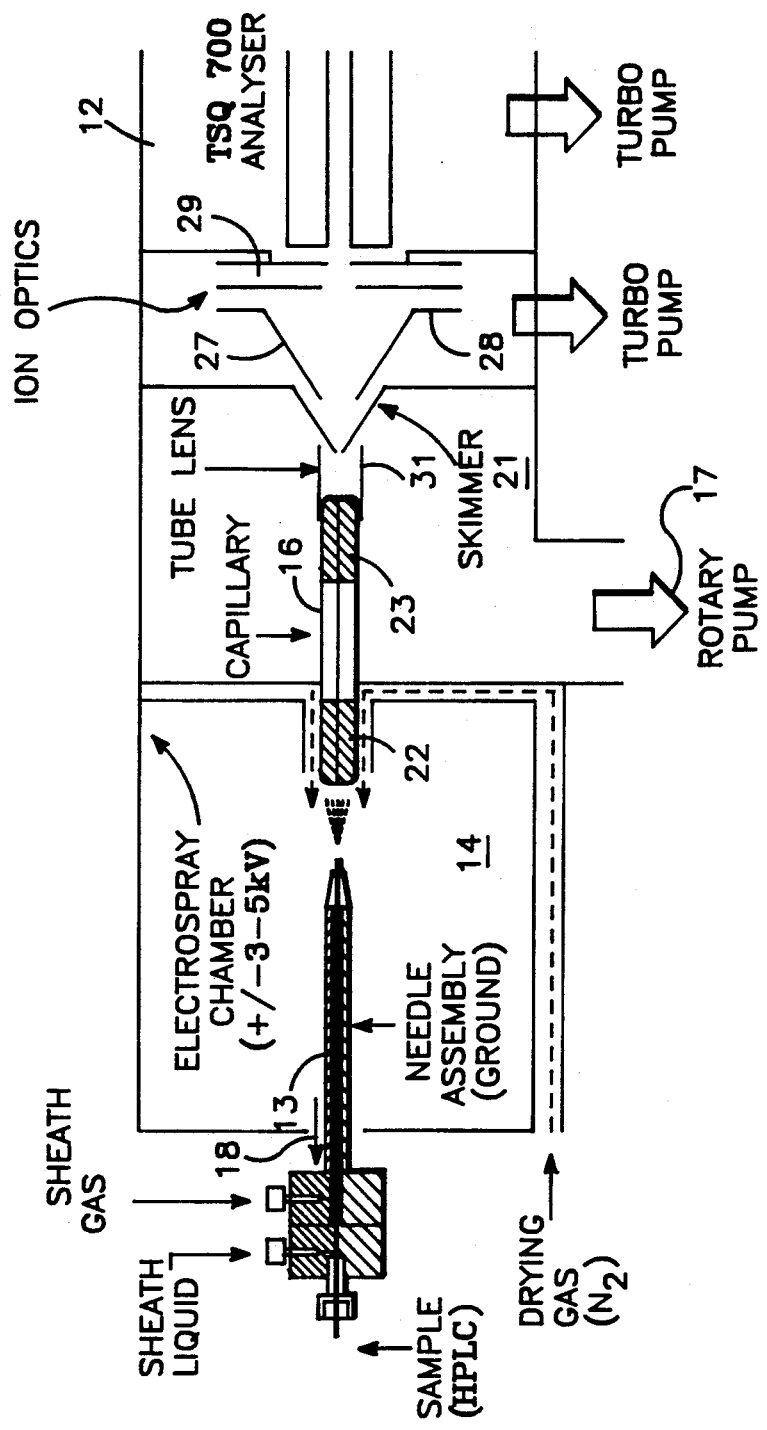
FIG. 1 shows an electrospray ion source coupled to an analyzing region via a capillary tube.

Referring to FIG. 1, an electrospray ion source 11 is schematically shown as associated with an analyzer chamber 12. The source includes an input needle assembly 13 which introduces a liquid sample into the ionization chamber 14. The needle includes an inner tube through which the liquid sample is introduced into the chamber. A second tube surrounds the first tube to define an annular region through which a sheath liquid is introduced for mixing with the sample liquid to reduce the surface tension and form droplets. An outer tube forms a second annulus through which a focusing gas is introduced to focus the droplets as they exit the needle towards a capillary tube 16.

The needle assembly 13 is not described in detail because it operates in accordance with well-known principles.

As previously explained, the needle, or capillary, is maintained at a high voltage with respect to the nearby surfaces forming the ionization chamber 14 and as the liquid is dispersed, the droplets or particles are charged by the voltage gradient at the tip of the capillary. The ionization mechanism involves the desorption at atmospheric pressure of ions from the fine electrically charged droplets. A counter-flow of gas indicated by the arrow 17 enhances the desorption process. The gas flows through chamber 14 past the end of the capillary 16 and exits the ionization chamber 14 as indicated schematically at 18.

A chamber 21 maintained at a lower pressure than the atmospheric pressure of the chamber 14 communicates with the ionization chamber via the capillary tube 16. Due to the differences in pressure, ions and gas are caused to flow through the capillary 16 into the chamber 21. A voltage gradient is formed along the insulated capillary by applying conductive sleeves 22, 23 and applying voltages thereto to provide a voltage gradient.

The end of the capillary is opposite a skimmer 26 which separates the low pressure region 21 from a lower pressure analyzer region 12. The skimmer includes a central orifice or aperture 27 which is aligned with the axis of the bore of the capillary. The skimmer is followed by ion optics which may comprise a second skimmer 28 and lenses 29, which direct ions into the analyzing chamber and into an associated mass analyzer.

As described above, as the ions leave the capillary, the pressure is still too high for direct introduction to an associated mass spectrometers; to overcome this, the gas is allowed to undergo a free expansion into the pumped chamber 21. The center of the flow is skimmed from the jet and allowed to pass into the mass spectrometer, while the edges are pumped away.

In accordance with this invention, a tube lens 31 is supported by the end of the capillary 16. The lens 31 is insulated from the end of the capillary by an insulating sleeve 32. The tube lens may be perforated as shown in FIGS. 1 and 2, or solid as shown in FIG. 3. A voltage is then applied between the conductive coating 23 on the capillary and the conductive tube lens. This voltage sets up electric fields within the tube which forces ions to the center of the expanding flow as indicated by the flow lines 34, FIGS. 2 and 3, while the gas can expand as shown by the flow lines 36. Then there is provided enriched ion flow in the center of the jet. The skimmer captures a higher percentage of the ions.

In summary, the function of the tube lens is to shape the electric fields in this region so that the ions are forced down the jet centerline, thus increasing the ion fraction captured by the mass spectrometer.

Not only is the ion beam intensified by the focusing action of the lens; but another beneficial effect is the divergence angle of the ion beam after the skimmer is narrower than expected from a free jet expansion. It is believed that this reduced divergence occurs because the strong electric field gradients on the upstream side of the skimmer propel the ions through the orifice at a velocity several times faster than the gas velocity. This means the ion trajectories downstream of the orifice are more influenced by these gradients than by the gas expansion from the skimmer. We have found that use of a tube lens has increased transmission of ions into the analyzer by at least a factor of three.

What is claimed is:

1. In an ion source of the type which includes an ionization chamber and an adjacent low pressure region including a skimmer having an orifice, a capillary tube having an axial bore communicating between the ionization chamber and the lower pressure region whereby ions and gases in said ionization chamber flow through said bore into said low pressure region and undergo jet flow expansion, the improvement comprising providing a conductive tube lens in the low pressure chamber in cooperative relationship with the capillary tube and applying a voltage to said tube lens to force ions in said jet flow to the center of the jet where they are captured by the skimmer.

2. An ion source as in claim 1 in which said ionization chamber includes means for electrospraying a sample to be analyzed.

3. An ion source as in claim 1 in which the lens is perforated.

4. An ion source as in claim 1 in which the lens is solid.

* * * * *